US00PP09261P

United States Patent [19]

Olesen et al.

[11] Patent Number: Plant 9,261

[45] Date of Patent: Aug. 29, 1995

[54] SHRUB ROSE PLANT NAMED 'POULMA'

[75] Inventors: Pernille Olesen; Mogens N. Olesen, both of Fredensborg, Denmark

[73] Assignee: Devor Nurseries, Inc., Watsonville, Calif.

[21] Appl. No.: 310,805

[22] Filed: Sep. 21, 1994

[51] Int. Cl.[6] ..... A01H 5/00

[52] U.S. Cl. ..... Plt./1

[58] Field of Search ..... Plt. 1, 22, 26

*Primary Examiner*—Howard J. Locker

*Attorney, Agent, or Firm*—Christie, Parker & Hale

[57] ABSTRACT

A new variety of shrub rose plant producing pink flowers.

SUMMARY OF THE INVENTION

The present invention relates to a new and distinct variety of rose plant of the shrub rose class which was originated by my crossing as seed and pollen parents two unnamed, unpatented, proprietary seedlings of our creation. The varietal denomination of this new rose is 'Poulma'.

Among the novel characteristics possessed by this new variety which distinguishes it from its parents are its vigorous, out-spreading, profuse flowering shrub growth habit producing attractively colored pink flowers.

Asexual reproduction by budding of the new variety as performed in Watsonville, Calif., shows that the foregoing and other distinguishing characteristics come true to form and are established and transmitted through succeeding propagations.

1 Drawing Sheet

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and cultivation conditions.

DESCRIPTION OF THE NEW VARIETY

'Poulma' is a very vigorous healthy out-growing plant, an extremely rich flowering bush which is very healthy, hardy and strong.

The following is a detailed description of my new variety, with color terminology in accordance with The Royal Horticultural Society Colour Chart (R.H.S.C.C.). The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class: Shrub.

The following information is from observations made of specimens grown outdoors in Watsonville, Calif. in the month of May.

FLOWER

Blooming habit: Recurrent.

A. Bud:

(1) *Size.*—Small.

(2) *Form.*—Round to slightly ovoid.

(3) *Color.*—As sepals divide, bud color is near 63A.

(4) *Sepals.*—Asymmetric with leaf-shaped tip, about cm in length, very foliaceous. Color: 144A outside with near 63A strip down center.

(5) *Peduncle.*—Length: About 4.5 to 5.4 cm. Aspect: Small prickles. Strength: Sturdy, erect. Color: Near 184A mixed with near 146D at top and bottom.

(6) *Bracts.*—Some near 147A. Form — broadly elliptical with pointed ends. Location in relation to flower — about 4.5 to 5.5 cm from calyx.

B. Bloom:

(1) *Size.*—About 7 to 8 cm.

(2) *Borne.*—Clusters and sprays of up to 32 to 42 blooms.

(3) *Form.*—Quartered.

(4) *Petalage.*—Number of petals under normal conditions — about 110 to 120.

(5) *Color.*—$\frac{1}{3}$ to $\frac{1}{2}$ open: Outer petals — top surface near 73D. Undersurface near 73D. Inner petals — top surface near 62A. Undersurface near 62A. Base of petals (point of attachment) near 6A. General tonality from a distance-pink. Fully open blooms: Outer petals — Top surface near 62C. Undersurface near 62C at top and near 62D at bottom. Inner petals — Top surface near 62C. Undersurface near 62C. Base of petals (point of attachment) near 155D. General tonality from a distance-pink. Color Change: As bloom ages color lightens to a softer lighter pink. Petal top surface — lighter pink with more white nearing bottom. Petal undersurface — lighter pink with more white nearing bottom. General tonality at a distance-light pale pink.

C. Petals:

(1) *Texture.*—Thick, smooth.

(2) *Appearance.*—Matte-like, outside, slightly velvety underneath.

(3) *Form.*—Broad with marginated apex.

(4) *Arrangement.*—Quartered.

(5) *Petaloids in Center.*—Many.

(6) *Persistence.*—Petals drop off cleanly.

(7) *Fragrance.*—None.
(8) *Lasting quality.*—Long lasting on plant.

REPRODUCTIVE ORGANS

Stamens, filaments and anthers:
*Arrangement.*—Irregularly arranged around styles (most inwardly).
*Stamens.*—Color — near 22A.
*Filaments.*—Color near 14B.
*Anthers.*—Color near 22A.
*Pollen.*—Color near 22A.

B. Styles: Bunched, even, medium length.
*Stigmas.*—Color — near 160A.

PLANT

A. Form: Grows as a mound.
B. Growth: Very vigorous.
*Height attained (first season).*—About 60 cm.
C. Foliage: Compound 3 to 7 leaflets.
(1) *Size.*—Medium.
(2) *Quantity.*—Abundant.
(3) *Color.*—New foliage: Upper side near 146A. Underside near 146B. Old foliage: Upper side near 146A to 147A. Underside — near 146B.
(4) *Shape.*—Cordate.
(5) *Texture.*—Upper side is glossy, smooth, slightly leathery and underside is dull, smooth and slightly leathery.
(6) *Edge.*—Serrated.

(7) *Serration.*—Denticulate.
(8) *Petiole color.*—Top surface — near 146A with near 178A on edges. Underside near 146C.
(9) *Stipules.*—Adnate with middle narrowing, bearded with glands on tip, glandular.
(10) *Auricle.*—Facing forward with glandular tips.
(11) *Rachis.*—Prickles underneath.
(12) *Resistance to disease.*—Very resistant to mildew, rust and blackspot.

D. Wood
(1) *New wood.*—Color — near 146C with tinges of near 187D. Bark — smooth with small prickles.
(2) *Old wood.*—Color — near 146B. Bark — smooth.

E. Thorns:
*Quantity (main stalk).*—Many.
*On laterals from stalk.*—Some.
*Forms.*—Slightly curved downwardly, near 187D when young.
*Lenght.*—medium.
*Position.*—Irregular.
*Prickles.*—None on main stems, profuse on laterals.

F. Winter hardiness: Very winter hardy in coastal California climate.

We claim:

1. A new and distinct variety of rose plant of the shrub rose class, substantially as shown and described.

* * * * *

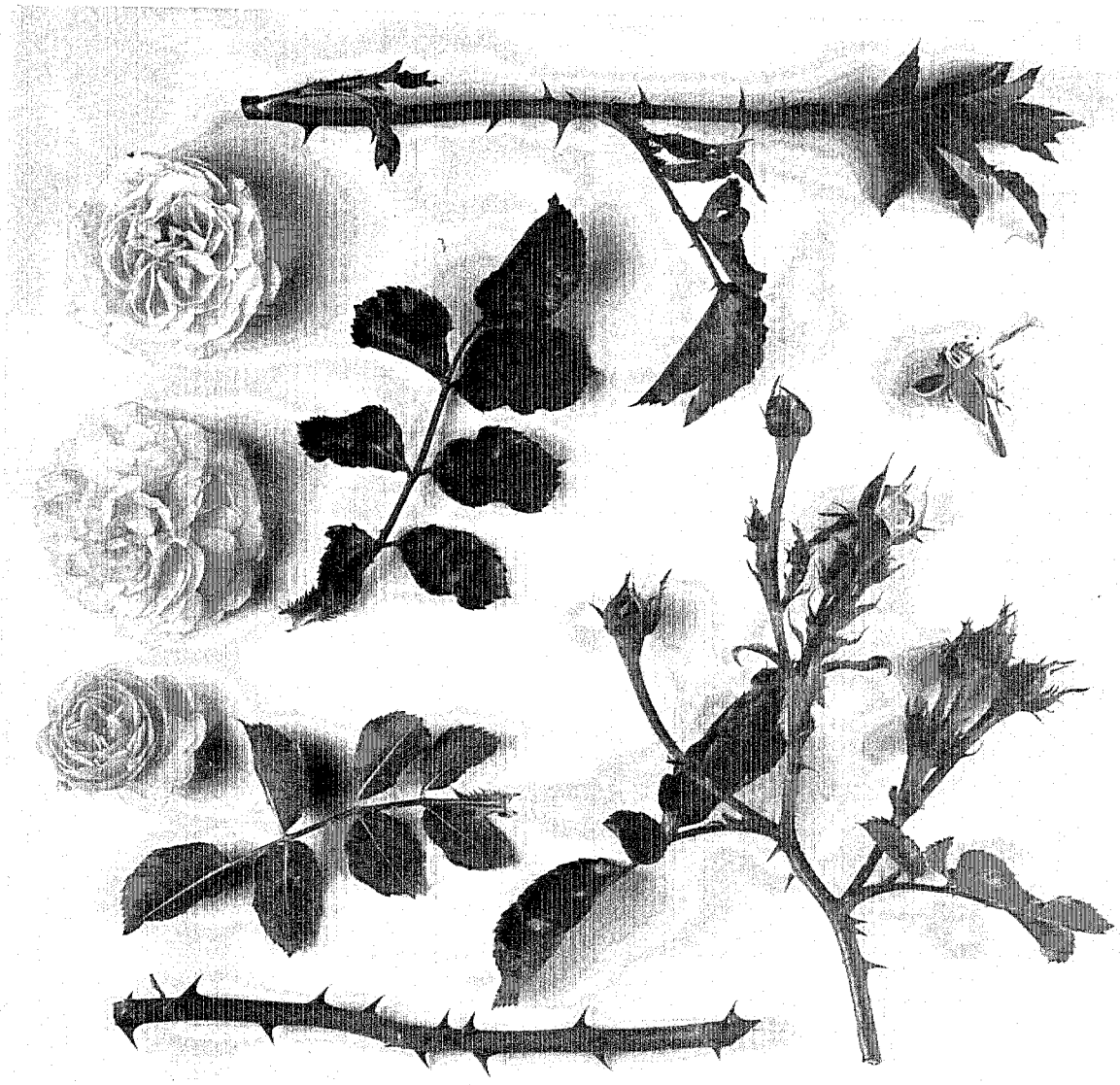

UNITED STATES PATENT AND TRADEMARK OFFICE

CERTIFICATE OF CORRECTION

PATENT NO. : Plant 9,261

DATED : August 29, 1995

INVENTOR(S) : Pernille Olesen; Mogens N. Olesen

It is certified that error appears in the above-indentified patent and that said Letters Patent is hereby corrected as shown below:

Column 2, line 2, before "cm" insert -- 1¾ --.

Column 2, line 23, change "blooms" to -- bloom --.

Column 3, line 5, before "Stamens" insert -- A. --.

Column 4, line 20, change "Lenght" to -- Length --.

Signed and Sealed this

Sixteenth Day of July, 1996

*Attest:*

*Attesting Officer*

Bruce Lehman

BRUCE LEHMAN

*Commissioner of Patents and Trademarks*